United States Patent [19]

Riza

[11] Patent Number: 5,501,692
[45] Date of Patent: Mar. 26, 1996

[54] LAPAROSCOPIC SUTURE SNARE

[76] Inventor: Erol D. Riza, 550 Riverside Dr., Rossford, Ohio 43460

[21] Appl. No.: 188,439

[22] Filed: Jan. 28, 1994

[51] Int. Cl.[6] .................................................. A61B 17/00
[52] U.S. Cl. .......................... 606/148; 606/139; 112/169
[58] Field of Search .................................. 606/139, 148, 606/144, 110, 113, 126, 133, 151, 187, 1, 222–227; 112/169, 80.03

[56] References Cited

U.S. PATENT DOCUMENTS

| | | | |
|---|---|---|---|
| 3,877,434 | 4/1975 | Ferguson et al. | 606/148 |
| 4,378,019 | 3/1983 | Yamada | 606/187 |
| 4,641,652 | 2/1987 | Hutterer et al. | 606/148 |
| 4,779,616 | 10/1988 | Johnson | 606/148 |
| 5,172,701 | 12/1992 | Leigh | 128/752 |
| 5,217,024 | 6/1993 | Dorsey et al. | 128/758 |
| 5,242,456 | 9/1993 | Nash et al. | 606/151 |
| 5,250,054 | 10/1993 | Li | 606/139 |
| 5,281,237 | 1/1994 | Gimpelson | 606/139 |
| 5,364,410 | 11/1994 | Failla et al. | 606/148 |
| 5,387,227 | 2/1995 | Grice | 606/144 |
| 5,405,354 | 4/1995 | Sarrett | 606/148 |

FOREIGN PATENT DOCUMENTS

| | | | |
|---|---|---|---|
| 969254 | 10/1982 | U.S.S.R. | 606/144 |

OTHER PUBLICATIONS

Product Brochure for RANFAC® Pneumoperitoneum Insufflation Needle.
Catalog page for Suture Retriever, Copyright 1988 Acufex Microsurgical, Inc.
"Endoscopic Technique For ACL Reconstruction With Pro-Trac® Tibial Guide", copyright 1991 Acufex MicroSurgical, Inc.

*Primary Examiner*—Stephen C. Pellegrino
*Assistant Examiner*—Jeffrey A. Schmidt
*Attorney, Agent, or Firm*—MacMillan, Sobanski & Todd

[57] ABSTRACT

An instrument for facilitating the use of sutures in laparoscopic surgical procedures includes a hollow housing defining an internal cavity. A plunger extends within the cavity of the housing and is supported therein for relative sliding movement between first and second axial positions. A spring disposed within the cavity urges the plunger to the first axial position relative to the housing. An introducer needle is secured to the housing and extends co-axially therefrom, terminating in an angled tip having a sharp point. An actuator tube is disposed within the introducer needle and is secured to the plunger for axial movement therewith relative to the housing. A flexible wire is disposed within portions of the actuator tube and is secured thereto for axial movement with the plunger. The wire is folded back over itself to form a looped end. When the plunger is in the first axial position, the looped end of the wire is withdrawn within the angled end of the introducer needle. When the plunger is moved to the second axial position, the looped end of the wire is extended outwardly from the angled end of the introducer needle. The looped end of the wire is permanently deformed in a diamond-like shape to facilitate usage when extended outwardly from the introducer needle.

54 Claims, 3 Drawing Sheets

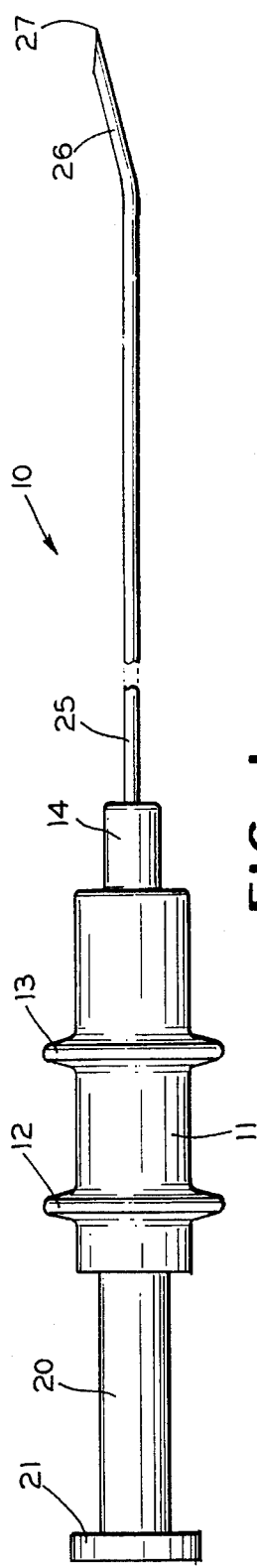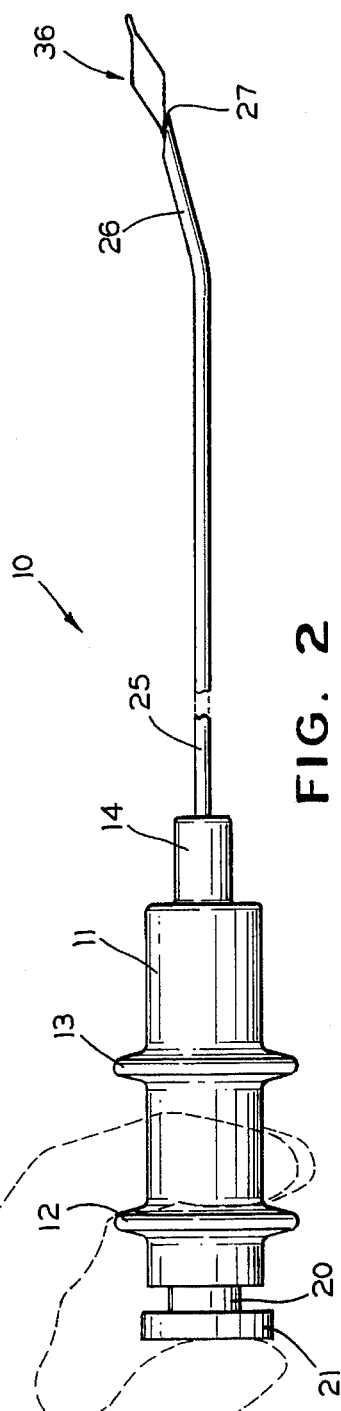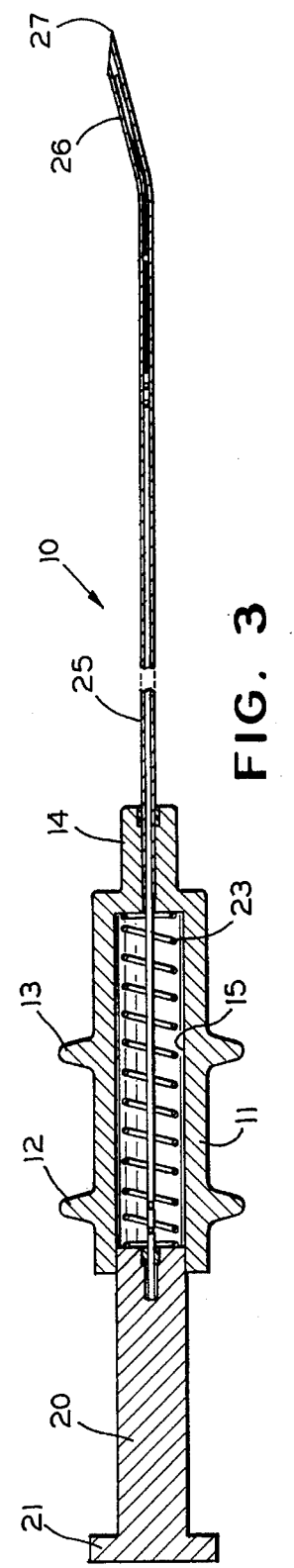

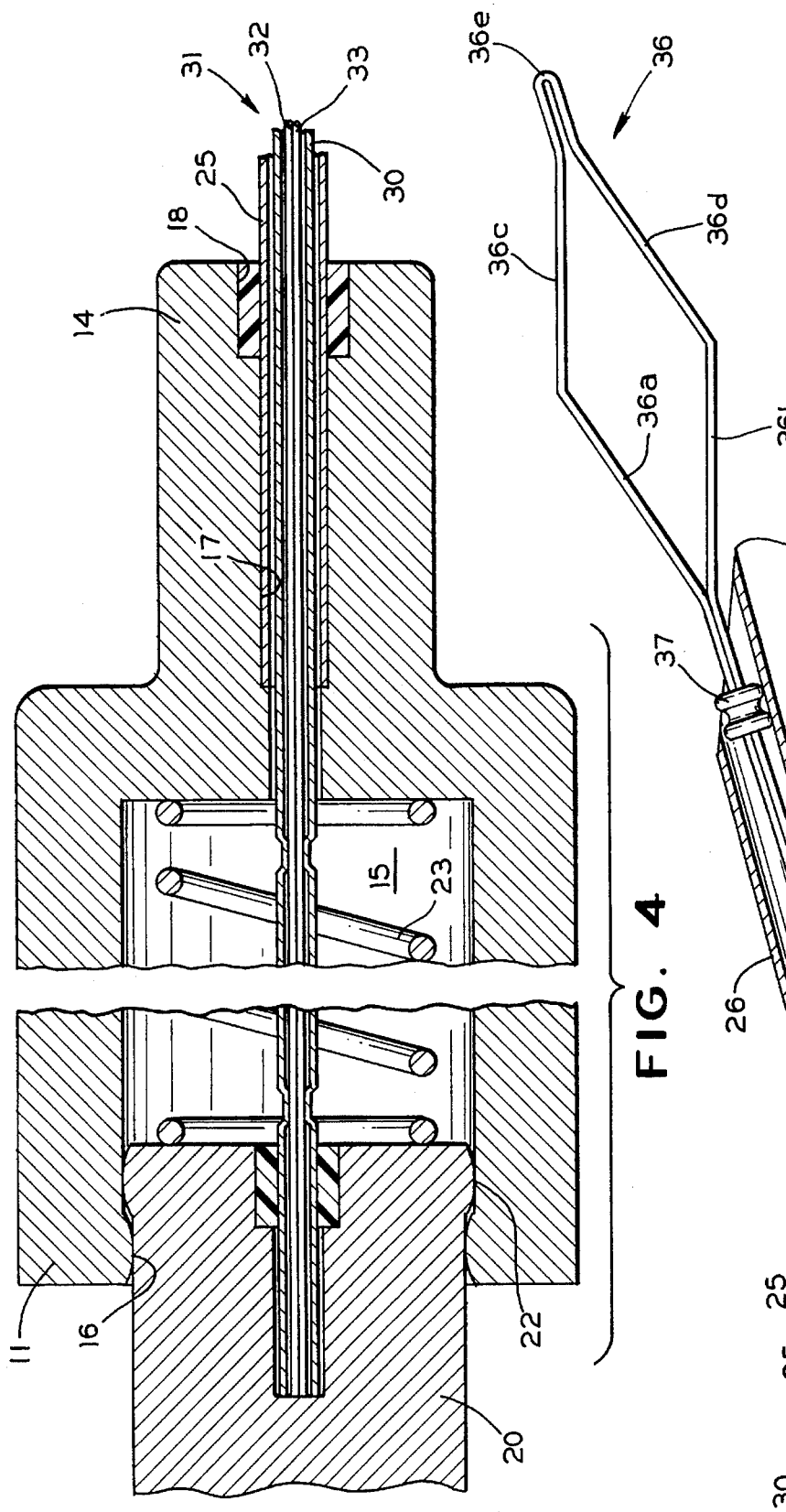

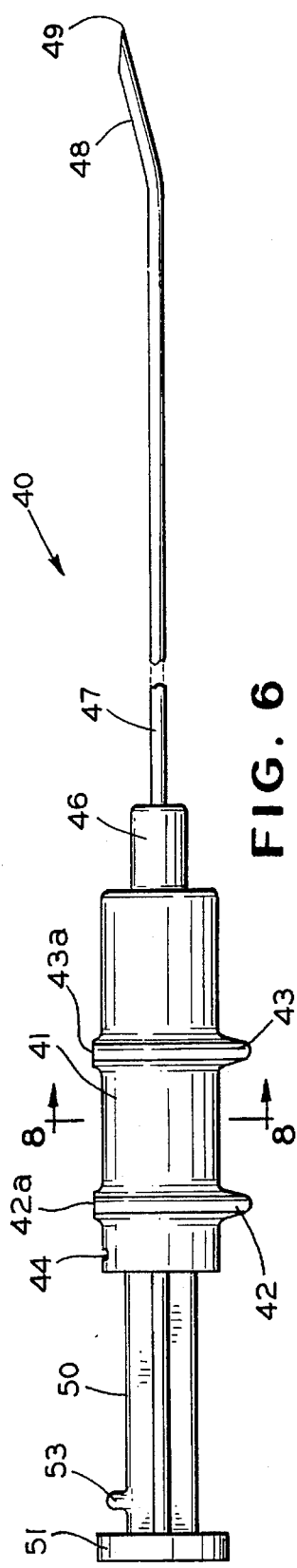
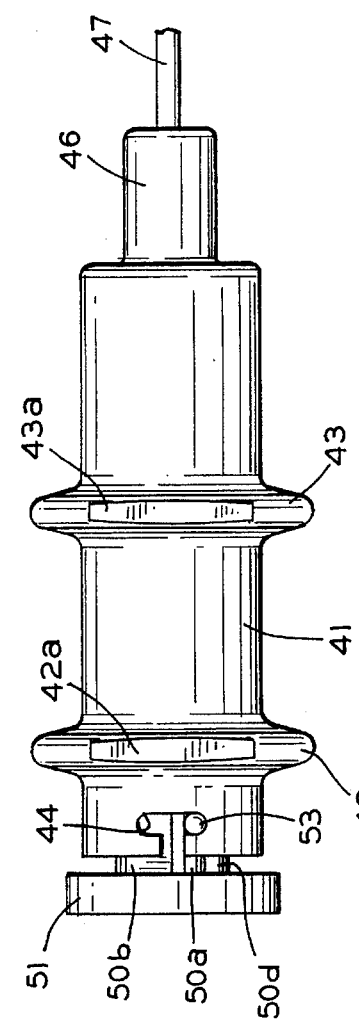
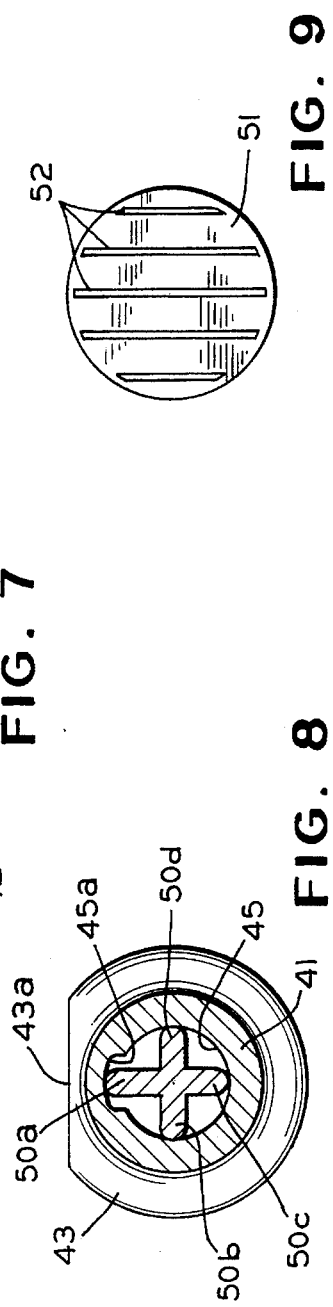
FIG. 6
FIG. 7
FIG. 8
FIG. 9

5,501,692

LAPAROSCOPIC SUTURE SNARE

BACKGROUND OF THE INVENTION

This invention relates in general to surgical instruments and in particular to a suture snare instrument for facilitating the use of sutures in laparoscopic surgical procedures.

Laparoscopic surgery is a relatively new operating technique which is much less invasive than conventional surgery and, therefore, may be performed using only a local anesthetic. Such laparoscopic surgery involves puncturing the abdominal wall and introducing an inert gas within the abdomen. The introduction of the inert gas expands the abdomen to facilitate access to the body parts requiring surgery and visual observation of the procedure. A hollow cylindrical tube is inserted into the puncture and is subsequently used as a conduit through which one or more elongated surgical instruments may be inserted within the abdomen. If desired, a plurality of punctures may be formed through the abdominal wall to facilitate the use of several surgical instruments.

During such laparoscopic surgeries, abdominal wall blood vessels may be injured and cause bleeding. When this occurs, it is necessary to stop such bleeding. Cauterization and the use of a folley-balloon-tamponade technique have been used in the past for stopping these abdominal wall bleeders during laparoscopic surgery. Although effective, these techniques are somewhat cumbersome and may result in undesirable delays or, at times, abandonment of the laparoscopic procedure. Sutures are well known for stopping external bleeding and are relatively quick and simple to employ. However, sutures are not usually employed in laparoscopic surgery because of difficulties in introducing and using them in the abdominal cavity. Thus, it would be desirable to provide an improved surgical instrument for facilitating the use of sutures in laparoscopic surgical procedures.

SUMMARY OF THE INVENTION

This invention relates to a suture snare instrument for facilitating the use of sutures in laparoscopic surgical procedures. The suture snare instrument includes a generally hollow cylindrical housing which is formed having a pair of circumferential flanges formed thereabout. The housing is formed having an internal cylindrical cavity which defines an internal diameter and extends from an opened end to a closed end. A plunger having an enlarged head extends within the cavity of the housing and is supported therein for relative sliding movement between first and second axial positions. A coiled spring disposed within the cavity urges the plunger to the first axial position relative to the housing. A tubular metallic introducer needle is secured to the housing and extends co-axially therefrom, terminating in an angled tip having a sharp point. A tubular metallic actuator tube is disposed within the introducer needle and is secured to the plunger for axial movement therewith relative to the housing. A flexible metallic wire is disposed within portions of the actuator tube and is secured thereto for axial movement with the plunger. The wire is folded back over itself to form a looped end. When the plunger is in the first axial position, the looped end of the wire is withdrawn within the angled end of the introducer needle. When the plunger is moved to the second axial position, the looped end of the wire is extended outwardly from the angled end of the introducer needle. The looped end of the wire is permanently deformed in a diamond-like shape to facilitate usage when extended outwardly from the introducer needle.

Various objects and advantages of this invention will become apparent to those skilled in the art from the following detailed description of the preferred embodiments, when read in light of the accompanying drawings.

BRIEF DESCRIPTION OF THE DRAWINGS

FIG. 1 is a side elevational view of a first embodiment of a laparoscopic suture snare instrument in accordance with this invention, wherein the plunger of the suture snare instrument is shown in a first axial position relative to the housing.

FIG. 2 is a side elevational view similar to FIG. 1, wherein the plunger of the suture snare instrument is shown in a second axial position relative to the housing.

FIG. 3 is a sectional elevational view of the suture snare instrument illustrated in FIG. 1.

FIG. 4 is an enlarged fragmentary sectional elevational view of the first and second ends of the housing of the suture snare instrument illustrated in FIG. 2.

FIG. 5 is an enlarged fragmentary sectional elevational view of the tip of the suture snare instrument illustrated in FIG. 2.

FIG. 6 is a side elevational view of a second embodiment of a laparoscopic suture snare instrument in accordance with this invention, wherein the plunger of the suture snare instrument is shown in a first axial position relative to the housing.

FIG. 7 is an enlarged top plan view of a portion of the suture snare instrument illustrated in FIG. 6.

FIG. 8 is a sectional elevational view taken along the line 8—8 of FIG. 6.

FIG. 9 is an end elevational view of the enlarged head of the plunger illustrated in FIG. 6.

DETAILED DESCRIPTION OF THE PREFERRED EMBODIMENTS

Referring now to the drawings, there is illustrated in FIGS. 1 through 3 a first embodiment of a laparoscopic suture snare instrument, indicated generally at 10, in accordance with this invention. The suture snare instrument 10 includes a generally hollow cylindrical housing 11 which is formed having a pair of circumferential flanges 12 and 13 formed thereabout. The first circumferential flange 12 is located adjacent to a first end of the housing 11, while the second circumferential flange 13 is located adjacent to a second end of the housing 11. Thus, the flanges 12 and 13 are axially spaced apart from one another, preferably by a distance of about three-fourths of one inch. As will be explained further below, the flanges 12 and 13 function as finger grips for grasping the housing 11. The housing 11 further includes a co-axial extension 14 provided at the second end thereof. The extension 14 is smaller in diameter than the housing 11 and is preferably formed integrally therewith. Preferably, the entire housing 11 is formed from a molded plastic material.

Referring now to FIGS. 3 and 4, the internal structure of the housing 11 is illustrated in detail. As shown therein, the housing 11 is formed having an internal cylindrical cavity 15. The cavity 15 defines an internal diameter and extends from an opened end at the first end of the housing 11 to a closed end adjacent the second end of the housing 11. A small radially inwardly extending ridge 16 is formed about the circumference of the opening defined at the first end of the housing 11 by the cavity 15. The purpose of this ridge 16 will be explained below. A co-axial passageway 17 extends from the cavity 15 through the extension 14 to a co-axial recess 18 formed in the second end of the housing 11. The purposes of the passageway 17 and the recess 18 will be explained below.

The suture snare instrument 10 also includes a plunger 20 having an enlarged head 21 formed at one end. The plunger 20 extends within the cavity 15 of the housing 11. The outer diameter of the plunger 20 is slightly smaller than the inner diameter of the cavity 15. Thus, the plunger 20 is supported within the housing 11 for relative axial sliding movement. As best shown in FIG. 4, a small radially outwardly extending ridge 22 is formed about the end of the plunger 20 opposite the head 21. The purpose of the ridge 22 will be explained below. As with the housing 11, the entire plunger 20 is preferably formed from a molded plastic material.

A coiled spring 23 or other resilient structure is disposed within the cavity 15. The ends of the spring 23 react against the inner end of the plunger 20 (adjacent to the ridge 22) and the closed end of the cavity 15. Thus, the spring 23 urges the plunger 20 to a first axial position relative to the housing 11, as shown in FIGS. 1 and 4. When in this position, the inner ridge 16 formed on the housing 11 engages the outer ridge 22 formed on the plunger 20. As a result, the plunger 20 is not ejected from the housing 11 under the urging of the spring 23. However, the plunger 20 can be removed from the housing 11 by manually applying a somewhat greater force, so as to compress the ridges 16 and 22. The plunger 20 may be moved to a second axial position within the housing 11 against the urging of the spring 23 by applying an appropriate force thereto. Typically, this force will be applied by squeezing with the fingers and thumb of a hand, such as shown in dotted lines in FIG. 2.

The suture snare instrument 10 further includes a tubular metallic introducer needle 25. The introducer needle 25 is secured to the axial extension 14 of the housing 11 and extends co-axially therefrom. Referring to FIG. 4, a first end of the introducer needle 25 extends through the recess 18 into a press fit relationship within the passageway 17 of the extension 14. Preferably, the recess 18 is then filled with an adhesive material to secure the introducer needle 25 to the housing 11. However, the first end of the introducer needle 25 may be fixed to the housing 11 by any suitable means, such as by integrally molding the housing 11 about the needle 25 or by a mechanical fastener. The second end of the introducer needle 25 is preferably (but not necessarily) angled, as shown at 26, relative to the longitudinal axis defined by the housing 11 at any desired angle. Also, the second end 26 of the introducer needle 25 is preferably provided with a sharp point 27.

The suture snare 10 further includes an elongated tubular metallic actuator tube 30 which is disposed within the introducer needle 25. A first end of the actuator tube 30 is secured to the inner end of the plunger 20 by any suitable means, such as those described above for securing the first end of the introducer needle 25 to the housing 11. Thus, the actuator tube 30 is secured to the plunger 20 for axial movement therewith relative to the housing 11. The actuator tube 30 extends through the cavity 15, the passageway 17, and into a portion of the introducer needle 25.

A flexible metallic wire 31 is disposed within portions of the actuator tube 30. As best shown in FIGS. 4 and 5, the wire 31 includes two end portions 32 and 33 which are located within the intermediate portion of the actuator tube 30. The two end portions 32 and 33 of the wire 31 are secured to the actuator tube 30. In the illustrated embodiment, the actuator tube 30 is crimped about the two end portions 32 and 33 of the wire 31 at two locations 34 and 35 to effect the connection therebetween. However, any conventional means may be used to connect the two end portions 32 and 33 of the wire 31 to the actuator tube 30. As a result, the entire wire 31 is secured to the actuator tube 30 for axial movement therewith when the plunger 20 is moved as described above.

Between the two end portions 32 and 33, the wire 31 is folded back over itself to form a looped end, indicated generally at 36 in FIG. 5. The looped end 36 of the wire 31 includes a pair of diverging leg portions 36a and 36b and a pair of converging leg portions 36c and 36d. The diverging leg portions 36a and 36b preferably define an angle of approximately thirty-five degrees therebetween. Similarly, the converging leg portions 36c and 36d also preferably define an angle of approximately thirty-five degrees therebetween. As a result, the angle between each of the diverging leg portions 36a and 36b and the associated one of the converging leg portions 36c and 36d is approximately one hundred forty-five degrees. Thus, the looped end 36 of the wire 31 is permanently deformed in a diamond like shape to facilitate usage when extended outwardly from the introducer needle 25, as described below.

The converging leg portion 36c and 36d are joined together by a narrow U-shaped bight portion 36e. The loop portion 36 can be formed in this manner by permanently deforming the appropriate portions of the metallic wire 31. A collar 37 is crimped about the wire 31 adjacent to the two diverging leg portions 36a and 36b. The purpose of the collar 37 will be explained below.

When the plunger 20 is in the first axial position illustrated in FIGS. 1, 3 and 4, the actuator tube 30 is located in a retracted position within the introducer needle 25. Thus, the wire 31 is also located in a retracted position within the introducer needle 25. As a result, the looped end 36 of the wire 31 is withdrawn within the angled end 26 of the introducer needle 25. When this occurs, the leg portions 36a, 36b, 36c, and 36d are resiliently deformed so as to lie essentially parallel with one another. This occurs not only because of the inherent flexibility of the wire 31, but also because of the permanently deformed shape of the looped end 36. As discussed above, the angle defined between each of the diverging leg portions 36a and 36b and the associated one of the converging leg portions 36c and 36d relatively large. Thus, the amount of deformation required to permit the looped end 36 to be withdrawn within the introducer needle 25 is relatively small. Also, the permanently deformed U-shaped bight portion 36e accommodates some flexing of the wire 31 and prevents it from becoming permanently deformed in other locations.

When the plunger 20 is moved to the second axial position illustrated in FIGS. 2 and 5, the actuator tube 30 is moved to an extended position relative to the introducer needle 25. Thus, the wire 31 is also located moved to an extended position relative to the introducer needle 25. As a result, the looped end 36 of the wire 31 is extended outwardly from the angled end 26 of the introducer needle 25. When this occurs, the resilient leg portions 36a, 36b, 36c, and 36d expand apart from one another to form the diamond shape configuration illustrated in FIG. 5. The collar 37 maintains the end portions 32 and 33 of the wire 31 adjacent to one another when extended from the angled end of the introducer needle 25.

Referring now to FIGS. 6 through 9, there is illustrated a second embodiment of a laparoscopic suture snare instrument, indicated generally at 40, in accordance with this invention. The suture snare instrument 40 includes a generally hollow cylindrical housing 41 generally similar in structure to the housing 11 of the first embodiment described above. The housing 41 is formed having a pair of circumferential flanges 42 and 43 formed thereabout. The first circumferential flange 42 is located adjacent to a first end of the housing 41, while the second circumferential flange 43 is located adjacent to a second end of the housing 41. Thus, the flanges 42 and 43 are axially spaced apart from one another, preferably by a distance of about three-fourths of one inch. As in the first embodiment described above, the flanges 42 and 43 function as finger grips for grasping the housing 41. The flanges 42 and 43 are formed having respective flats 42*a* and 43*a* in the upper portions thereof, for a purpose which will be explained below.

The upper portion of the housing 41 is formed having a generally T-shaped slot 44. The stem portion of the T-shaped slot 44 extends from the first end of the housing 41 axially toward the first circumferential flange 42. The cross portion of the T-shaped slot 44 extends transversely from the end of the stem portion. The slot 44 is formed completely through the housing 41 from the exterior surface thereof to an internal cavity 45 (see FIG. 8) defined therein. The purpose of the slot 44 will be discussed below. As with the housing 11 described above, the housing 41 also includes a co-axial extension 46 provided at the second end thereof. The extension 46 is smaller in diameter than the housing 41 and is preferably formed integrally therewith from a molded plastic material. Also, an introducer needle 47, similar to the introducer needle 25 discussed above, is secured to the axial extension 47 of the housing 41 and extends co-axially therefrom.

As in the first embodiment discussed above, the introducer needle 47 of the suture snare instrument 40 includes an angled end portion 48 and a sharp tip 49. The angled end portion 48 preferably extends upwardly in alignment with the upper flats 42*a* and 43*a* respectively formed on the flanges 42 and 43. Thus, the flats 42*a* and 43*a* provide the user of the suture snare instrument 40 with a tactile indication of the relative orientation of the angled end 48 of the introducer needle 47.

As best shown in FIG. 8, and similar to the internal cavity 15 described above, the internal cavity 45 of the housing 41 defines an internal diameter and extends from an opened end at the first end of the housing 41 to a closed end adjacent the second end of the housing 41. Unlike the cavity 15, however, an axially extending recess 45*a* is formed in the upper portion of the inner surface of the housing 41. The recess 45*a* extends from the open end of the housing 41 throughout most or all of the cavity 45. The axially extending sides of the recess 45*a* define an arc relative to the longitudinal axis of the housing 41. Preferably, the magnitude of this arc is approximately twenty-eight degrees. The purpose of the recess 45*a* will be discussed below.

The suture snare instrument 40 also includes a plunger 50 having an enlarged head 51 formed at one end. As best shown in FIG. 9, the head 51 is formed having a plurality of parallel raised ribs 52 on the outer face thereof. The purpose of the raised ribs 52 will be discussed below. The plunger 50 extends within the cavity 45 of the housing 41. As best shown in FIG. 8, the plunger 50 is formed generally in the shape of a cross having four radially outwardly extending web portions 50*a*, 50*b*, 50*c*, and 50*d*. The ends of the web portions 50*a*, 50*b*, 50*c*, and 50*d* abut the inner surface of the housing 41 to support the plunger 50 therein for relative axial sliding movement. The web portion 50*a* is slightly longer in length than the remaining web portions 50*b*, 50*c*, and 50*d*. As a result, the web portion 50*a* extends into the recess 45*a* formed in the inner surface of the housing 41. The cooperation of the web portion 50*a* with the recess 45*a* limits the ability of the plunger 50 to rotate relative to the housing 41 to the arc defined by the longitudinal sides of the recess 45*a*.

An upstanding pin 53 is provided on the outer end of the web portion 50*a* adjacent to the enlarged head 51 of the plunger 50. The pin 53 is preferably formed as an integral part of the plunger 50. The pin 53 is sized to fit into the slot 44 formed in the housing 41, as illustrated in FIG. 7, when the plunger 50 is moved to the second axial position relative to the housing 41. The cooperation of the web portion 50*a* of the plunger 50 with the recess 45*a* of the housing 41 maintains the pin 53 in axial alignment with the stem portion of the slot 44. As a result, the plunger 50 can easily be depressed within the housing 41 to the second axial position.

In some instances, it may be desirable to lock the plunger 50 in the second axial position. To accomplish this, the plunger 50 is rotated relative to the housing 41 so as to cause the pin 53 to be moved into the cross portion of the slot 44, as shown in FIG. 7. This relative rotation movement is facilitated by the raised ribs 52 provided on the enlarged head 51 of the plunger 50. The ribs 52 provide for increased frictional engagement by the thumb of the user for accomplishing this relative rotational movement. Preferably, rotation of approximately thirteen degrees will be sufficient to move the pin 53 into the cross portion of the slot 44. The remaining portions of the suture snare instrument 40 are identical to the suture snare instrument 10 described above and, therefore, require no further explanation.

The suture snare instruments 10 and 40 are preferably utilized to insert and tie sutures in a laparoscopic surgical procedure. To accomplish this, the housing 11 is supported by the index and middle fingers of one hand (shown in dotted lines in FIG. 2) extending between the flanges 12 and 13. The thumb of the same hand is used to selectively depress the plunger 20 for movement between the first and second axial positions relative to the housing 11. When the plunger 20 is depressed, the looped end 36 is extended from the angled end 26 of the introducer needle 25 and expands into the illustrated diamond shape. When so extended and expanded, one end of a suture (not shown) can be passed through the looped end 36. Then, the plunger 20 released so that the spring 23 urges it back to the first axial position. As a result, the looped end 36 is retracted within the angled end 26 of the introducer needle 25. The end of the suture is also retracted within the angled end 26 of the introducer needle when this occurs. Thus, the suture is frictionally captured by the suture snare instrument 10.

Then, the suture snare instrument 10 is manipulated such that the sharp angled end 26 of the introducer needle 25 is passed through a selected portion of body tissue, together with the end of the suture engaged thereby. Next, the plunger 20 is moved to the second axial position, which again extends the looped end 36 of the wire 31 outwardly from the angled end 26 of the introducer needle 25. Again, the looped end 36 expands to the above-discussed diamond shape, releasing the frictional engagement of the end of the suture. The suture can be grasped by another surgical instrument, such as a pair of small grippers, and removed completely from within the extended loop portion 36 of the wire 31. Then, the plunger 20 can be released to retract the looped end 36 of the wire 31 back within the angled end 26 of the introducer needle 25. Finally, the introducer needle 25 is withdrawn from the body tissue, allowing the suture to be tied in a conventional manner. The suture snare instrument 40 operates in generally the same manner as the suture snare instrument 10, but is further provided with the slot 44 and pin 53 for maintaining the looped end 36 of the wire 31 in the extended position.

In accordance with the provisions of the patent statutes, the principle and mode of operation of the present invention have been explained and illustrated in its preferred embodiments. However, it must be understood that the present invention may be practiced otherwise than as specifically explained and illustrated without departing from its spirit or scope.

What is claimed is:

1. A suture snare instrument comprising:
   a hollow housing defining an internal cavity;
   an introducer needle having a first end secured to said hollow housing and a second end, said second end terminating in a sharp point to permit the insertion thereof through body tissue;
   a plunger extending within said hollow housing and supported for sliding movement relative thereto between first and second positions;
   a spring engaged with said plunger to urge said plunger toward said first position and
   a wire disposed within said introducer needle and connected to said plunger for movement therewith, said wire having a looped end which is retracted within said second end of said introducer needle when said plunger is in said first position and which extends outwardly from said second end of said introducer needle when said plunger is in said second position.

2. The suture snare instrument defined in claim 1 wherein said spring is disposed within said internal cavity of said hollow housing and reacts between said hollow housing and said plunger to urge said plunger toward said first position.

3. The suture snare instrument defined in claim 1 further including cooperating structures formed on said hollow housing and said plunger for selectively retaining said plunger in said second position.

4. The suture snare instrument defined in claim 3 wherein said cooperating structures include a slot formed in said hollow housing and a pin formed on said plunger.

5. The suture snare instrument defined in claim 4 wherein said plunger is rotatable relative to said hollow housing when said plunger is in said second position such that said pin is selectively received within said slot to retain said plunger in said second position.

6. The suture snare instrument defined in claim 5 wherein said slot includes a first portion, through which said pin is moved when said plunger is moved between said first and second positions relative to said hollow housing, and a second portion, through which said pin is moved when said plunger is rotated relative to said hollow housing when in said second position.

7. The suture snare instrument defined in claim 6 wherein said pin is moved through said second portion of said slot when said plunger is rotated in a first rotational direction relative to said hollow housing, and wherein said slot further includes a third portion, through which said pin is moved when said plunger is rotated in a second rotational direction relative to said hollow housing.

8. The suture snare instrument defined in claim 1 wherein said second end of said introducer needle extends at an angle relative to said first end.

9. The suture snare instrument defined in claim 8 further including a flange extending outwardly from said hollow housing and having a flat formed thereon for providing a tactile indication of said angle of said second end of said introducer needle relative to said first end.

10. The suture snare instrument defined in claim 1 further including cooperating structures formed on said hollow housing and said plunger for preventing said plunger from being ejected from said housing.

11. The suture snare instrument defined in claim 10 wherein said cooperating structures include an inwardly extending ridge formed on said hollow housing and an outwardly extending ridge formed on said plunger.

12. The suture snare instrument defined in claim 11 wherein said inwardly extending ridge extends circumferentially about said hollow housing and wherein said outwardly extending ridge extends circumferentially about said plunger.

13. The suture snare instrument defined in claim 1 wherein said looped end of said wire includes a pair of diverging leg portions and a pair of converging leg portions.

14. The suture snare instrument defined in claim 13 wherein said diverging leg portions define an interior angle of about thirty-five degrees, and wherein said converging leg portions define an interior angle of about thirty-five degrees.

15. The suture snare instrument defined in claim 13 wherein said looped end of said wire includes a U-shaped bight portion joining said converging leg portions.

16. The suture snare instrument defined in claim 1 further including cooperating structures formed on said hollow housing said plunger for limiting relative rotational movement therebetween.

17. The suture snare instrument defined in claim 16 wherein said cooperating structures include a recess formed in a surface of said hollow housing and a web portion formed on said plunger which extends into said recess for limiting relative rotational movement therebetween.

18. The suture snare instrument defined in claim 1 further including an enlarged head formed on said plunger having a plurality of raised fibs formed thereon.

19. A suture snare instrument comprising:
   a hollow housing defining an internal cavity;
   an introducer needle having a first end secured to said hollow housing and a second end which extends at an angle relative to said first end;
   a plunger extending within said hollow housing and supported for sliding movement relative thereto between first and second positions;
   a wire disposed within said introducer needle and connected to said plunger for movement therewith, said wire having a looped end which is retracted within said second end of said introducer needle when said plunger is in said first position and which extends outwardly from said second end of said introducer needle when said plunger is in said second position; and
   a flange extending outwardly from said hollow housing and having a flat formed thereon for providing a tactile indication of the angle at which said second end of said introducer needle extends relative to said first end thereof.

20. The suture snare instrument defined in claim 19 further including a spring engaged with said plunger for urging said plunger toward said first position.

21. The suture snare instrument defined in claim 20 wherein said spring is disposed within said internal cavity of said hollow housing and reacts between said hollow housing and said plunger for urging said plunger toward said first position.

22. The suture snare instrument defined in claim 19 further including cooperating structures formed on said hollow housing and said plunger for selectively retaining said plunger in said second position.

23. The suture snare instrument defined in claim 22 wherein said cooperating structures include a slot formed in said hollow housing and a pin formed on said plunger.

24. The suture snare instrument defined in claim 23 wherein said plunger is rotatable relative to said hollow housing when said plunger is in said second position such that said pin is selectively received within said slot to retain said plunger in said second position.

25. The suture snare instrument defined in claim 24 wherein said slot includes a first portion, through which said pin is moved when said plunger is moved between said first and second positions relative to said hollow housing, and a second portion, through which said pin is moved when said plunger is rotated relative to said hollow housing when in said second position.

26. The suture snare instrument defined in claim 25 wherein said pin is moved through said second portion of said slot when said plunger is rotated in a first rotational direction relative to said hollow housing, and wherein said slot further includes a third portion, through which said pin is moved when said plunger is rotated in a second rotational direction relative to said hollow housing.

27. The suture snare instrument defined in claim 19 further including cooperating structures formed on said hollow housing and said plunger for preventing said plunger from being ejected from said housing.

28. The suture snare instrument defined in claim 27 wherein said cooperating structures include an inwardly extending ridge formed on said hollow housing and an outwardly extending ridge formed on said plunger.

29. The suture snare instrument defined in claim 28 wherein said inwardly extending ridge extends circumferentially about said hollow housing and wherein said outwardly extending ridge extends circumferentially about said plunger.

30. The suture snare instrument defined in claim 19 wherein said looped end of said wire includes a pair of diverging leg portions and a pair of converging leg portions.

31. The suture snare instrument defined in claim 30 wherein said diverging leg portions define an interior angle of about thirty-five degrees, and wherein said converging leg portions define an interior angle of about thirty-five degrees.

32. The suture snare instrument defined in claim 30 wherein said looped end of said wire includes a U-shaped bight portion joining said converging leg portions.

33. The suture snare instrument defined in claim 19 further including cooperating structures formed on said hollow housing said plunger for limiting relative rotational movement therebetween.

34. The suture snare instrument defined in claim 33 wherein said cooperating structures include a recess formed in a surface of said hollow housing and a web portion formed on said plunger which extends into said recess for limiting relative rotational movement therebetween.

35. The suture snare instrument defined in claim 19 further including an enlarged head formed on said plunger having a plurality of raised ribs formed thereon.

36. A suture snare instrument comprising:
a hollow housing defining an internal cavity;
an introducer needle having a first end secured to said hollow housing and a second end;
a plunger extending within said hollow housing and supported for sliding movement relative thereto between first and second positions;
a wire disposed within said introducer needle and connected to said plunger for movement therewith, said wire having a looped end which is retracted within said second end of said introducer needle when said plunger is in said first position and which extends outwardly from said second end of said introducer needle when said plunger is in said second position; and
a slot formed in one of said hollow housing and said plunger and a pin provided on the other one of said hollow housing and said plunger, said slot and said pin cooperating to selectively retain said plunger in said second position.

37. The suture snare instrument defined in claim 36 further including a spring engaged with said plunger to urge said plunger toward said first position.

38. The suture snare instrument defined in claim 37 wherein said spring is disposed within said internal cavity of said hollow housing and reacts between said hollow housing and said plunger to urge said plunger toward said first position.

39. The suture snare instrument defined in claim 36 wherein said slot is formed in said hollow housing and said pin is provided on said plunger.

40. The suture snare instrument defined in claim 39 wherein said plunger is rotatable relative to said hollow housing when said plunger is in said second position such that said pin is selectively received within said slot to retain said plunger in said second position.

41. The suture snare instrument defined in claim 40 wherein said slot includes a first portion, through which said pin is moved when said plunger is moved between said first and second positions relative to said hollow housing, and a second portion, through which said pin is moved when said plunger is rotated relative to said hollow housing when in said second position.

42. The suture snare instrument defined in claim 41 wherein said pin is moved through said second portion of said slot when said plunger is rotated in a first rotational direction relative to said hollow housing, and wherein said slot further includes a third portion, through which said pin is moved when said plunger is rotated in a second rotational direction relative to said hollow housing.

43. The suture snare instrument defined in claim 36 wherein said second end of said introducer needle extends at an angle relative to said first end.

44. The suture snare instrument defined in claim 43 further including a flange extending outwardly from said hollow housing and having a flat formed thereon for providing a tactile indication of said angle of said second end of said introducer needle relative to said first end.

45. The suture snare instrument defined in claim 36 further including cooperating structures formed on said hollow housing and said plunger for preventing said plunger from being ejected from said housing.

46. The suture snare instrument defined in claim 45 wherein said cooperating structures include an inwardly extending ridge formed on said hollow housing and an outwardly extending ridge formed on said plunger.

47. The suture snare instrument defined in claim 46 wherein said inwardly extending ridge extends circumferentially about said hollow housing and wherein said outwardly extending ridge extends circumferentially about said plunger.

48. The suture snare instrument defined in claim 36 wherein said looped end of said wire includes a pair of diverging leg portions and a pair of converging leg portions.

49. The suture snare instrument defined in claim 48 wherein said diverging leg portions define an interior angle of about thirty-five degrees, and wherein said converging leg portions define an interior angle of about thirty-five degrees.

50. The suture snare instrument defined in claim 49 wherein said looped end of said wire includes a U-shaped bight portion joining said converging leg portions.

51. The suture snare instrument defined in claim 36 further including cooperating structures formed on said hollow housing said plunger for limiting relative rotational movement therebetween.

52. The suture snare instrument defined in claim 51 wherein said cooperating structures include a recess formed in a surface of said hollow housing and a web portion formed on said plunger which extends into said recess for limiting relative rotational movement therebetween.

53. The suture snare instrument defined in claim 36 further including an enlarged head formed on said plunger having a plurality of raised ribs formed thereon.

54. The suture snare instrument defined in claim 36 wherein said second end of said introducer needle terminates in a sharp point to permit the insertion thereof through body tissue.

* * * * *